US012582146B2

(12) United States Patent
Nishitani

(10) Patent No.: US 12,582,146 B2
(45) Date of Patent: *Mar. 24, 2026

(54) ANGIOTENSIN-CONVERTING ENZYME INHIBITOR, BLOOD PRESSURE-LOWERING AGENT, AND BEVERAGES AND FOOD PRODUCTS

(71) Applicant: MARUZEN PHARMACEUTICALS CO., LTD., Hiroshima (JP)

(72) Inventor: Yosuke Nishitani, Hiroshima (JP)

(73) Assignee: MARUZEN PHARMACEUTICALS CO., LTD., Hiroshima (JP)

( * ) Notice: Subject to any disclaimer, the term of this patent is extended or adjusted under 35 U.S.C. 154(b) by 767 days.

This patent is subject to a terminal disclaimer.

(21) Appl. No.: 17/764,666

(22) PCT Filed: Sep. 2, 2020

(86) PCT No.: PCT/JP2020/033216

§ 371 (c)(1),
(2) Date: Mar. 29, 2022

(87) PCT Pub. No.: WO2021/065307

PCT Pub. Date: Apr. 8, 2021

(65) Prior Publication Data

US 2022/0330595 A1 Oct. 20, 2022

(30) Foreign Application Priority Data

Sep. 30, 2019 (JP) ................................ 2019-180155

(51) Int. Cl.

*A23L 33/10* (2016.01)
*A61K 31/192* (2006.01)
*A61P 9/12* (2006.01)

(52) U.S. Cl.

CPC ............ *A23L 33/10* (2016.08); *A61K 31/192* (2013.01); *A61P 9/12* (2018.01)

(58) Field of Classification Search

CPC .......... A23L 33/10; A61P 9/12; A61K 31/192
See application file for complete search history.

(56) References Cited

U.S. PATENT DOCUMENTS

| | | | |
|---|---|---|---|
| 2002/0051810 A1 | 5/2002 | Suzuki et al. | |
| 2004/0043057 A1 | 3/2004 | Suzuki et al. | |
| 2004/0198807 A1 | 10/2004 | Suzuki et al. | |

FOREIGN PATENT DOCUMENTS

| | | | | |
|---|---|---|---|---|
| JP | 2002-053464 | A | | 2/2002 |
| JP | 2006-342134 | A | | 12/2006 |
| JP | 2008-239521 | A | | 10/2008 |
| JP | 2012-144532 | A | | 8/2012 |
| JP | 2013-043839 | A | | 3/2013 |
| JP | 2018/016618 | | * | 2/2018 |
| JP | 2018-016618 | A | | 2/2018 |
| WO | WO2014048888 | | * | 3/2014 |

OTHER PUBLICATIONS

Cleto et al. Experimental and Molecular Medicine, vol. 39(3)327-334, 2007.*
Kloet et al. Pysiol Behav (2010) vol. 100(5): 525-534.*
Kagaku to Seibutsu, vol. 53, No. 4. (2015) p. 228-235.
International Search Report dated Oct. 10, 2020, issued in corresponding International Patent Application No. PCT/JP2020/033216 (and English Machine Translation).

* cited by examiner

*Primary Examiner* — Shirley V Gembeh
(74) *Attorney, Agent, or Firm* — Posz Law Group, PLC

(57) ABSTRACT

This angiotensin-converting enzyme inhibitor and this blood pressure-lowering agent contain a compound represented by formula (I) as an active ingredient. These beverages and food products for inhibiting an angiotensin-converting enzyme and these beverages and food products for lowering blood pressure are characterized by containing a compound represented by formula (I). As a result, provided are an angiotensin-converting enzyme inhibitor and blood pressure-lowering agent that have an excellent angiotensin-converting enzyme-inhibiting effect and blood pressure-lowering effect. Furthermore, provided are beverages and food products suitable for inhibition of an angiotensin-converting enzyme and lowering of blood pressure.

(I)

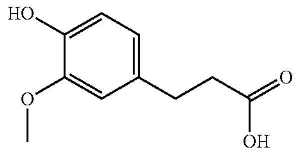

12 Claims, No Drawings

ANGIOTENSIN-CONVERTING ENZYME INHIBITOR, BLOOD PRESSURE-LOWERING AGENT, AND BEVERAGES AND FOOD PRODUCTS

CROSS REFERENCE TO RELATED APPLICATIONS

This application is a U.S. national stage application of PCT/JP2020/033216 filed on Sep. 2, 2020 and is based on Japanese Patent Application No. 2019-180155 filed on Sep. 30, 2019, the contents of which are incorporated herein by reference.

TECHNICAL FIELD

The present invention relates to an angiotensin-converting enzyme inhibitor, a blood pressure-lowering agent and beverages and food products.

BACKGROUND ART

High blood pressure has been, along with obesity and smoking, a risk factor of lifestyle related disease. Continuous hypertensive state may cause organopathy, such as heart failure and myocardial infraction in heart, nephropathy and renal dysfunction in kidneys, and obstructive and dissociated arterial diseases. Therefore, there is a high demand for ameliorating hypertension in the society.

As a factor related to blood pressure elevation, angiotensin I-converting enzyme (also referred to as "ACE" in the present specification) has been known. The angiotensin-converting enzyme is a dicarboxypeptidase (molecular weight 147 kDa) having zinc at an active center and has two catalytically active domains (C and N domains).

The C domain of the angiotensin-converting enzyme catalyzes a reaction of generating angiotensin II by isolating C-terminal dipeptide of angiotensin I. Angiotensin II contracts vascular smooth muscle via receptor (AT1R) being present on blood vessel wall and, consequently, causes blood pressure elevation. Furthermore, angiotensin II prompts production of aldosterone from adrenal cortex and accelerates reabsorption of sodium in kidneys, which causes blood pressure elevation (Non-Patent Document 1).

Accordingly, it is considered that blood pressure can be lowered by inhibiting the angiotensin-converting enzyme. As those having an effect of inhibiting the angiotensin-converting enzyme, a decomposition product from pyloric appendage of mackerel, which is fish protein, (Patent Document 1) has been reported.

PRIOR ART DOCUMENTS

Patent Documents

[Patent Document 1] Japanese Patent Publication (Kokai) No. 2013-043839

Non-Patent Document

[Non-Patent Document 1] KAGAKU TO SEIBUTSU pp. 228-235, Vol. 53, Issue 4, 2015

SUMMARY OF THE INVENTION

Problem to be Solved by the Invention

The present invention has its object to provide an angiotensin-converting enzyme inhibitor, a blood pressure-lowering agent and beverages and food products.

Solution to the Problem

To attain the object above, an angiotensin-converting inhibitor and a blood pressure-lowering agent of the present invention are characterized by containing as an active ingredient a compound represented by formula (I) below.

Also, angiotensin-converting enzyme inhibiting beverages and food products and blood pressure-lowering beverages and food products of the present invention are characterized by containing the compound represented by formula (I) below.

[Chemical Formula 1]

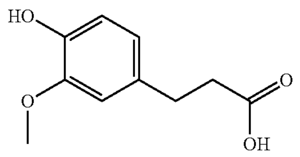

(I)

Effect of the Invention

According to the present invention, as a result of containing the compound represented by formula (I) above as an active ingredient, it is possible to provide an angiotensin-converting enzyme inhibitor and a blood pressure-lowering agent having excellent effects of inhibiting an angiotensin-converting enzyme and lower blood pressure. By blending the compound represented by formula (I) above, it is furthermore possible to provide beverages and food products suitable for the purposes above.

MODE(S) FOR CARRYING OUT THE INVENTION

Below, embodiment(s) of the present invention will be explained.

An angiotensin-converting enzyme inhibitor and a blood pressure-lowering agent according to the present embodiment contain a compound represented by formula (I) below. Also, angiotensin-converting enzyme inhibiting beverages and food products and blood pressure-lowering beverages and food products according to the present embodiment contain the compound represented by formula (I) below.

[Chemical Formula 2]

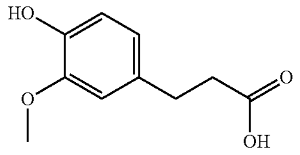

(I)

The compound represented by formula (I) above is a cinnamic acid derivative also called 3-(4-hydroxy-3-methoxyphenyl)propionic acid. Hereinafter, the compound represented by formula (I) above will be also referred to as compound (I) in this specification.

The compound (I) may be produced from plant extracts containing the compound (I) through isolating and purifying. Such plant extracts containing the compound (I) may be obtained by generally-used methods of extracting from plants. For example, rice, barley, wheat, soybeans, azuki beans and corn, may be mentioned as plants containing the compound (I).

The compound (I) may be also produced, for example, by fermenting 3-(4-hydroxy-3-methoxyphenyl)propenoic acid, derivatives thereof or a composition containing these (for example, ground plants or plant extracts) by microorganism having phenolic acid reductases, converting 3-(4-hydroxy-3-methoxyphenyl)propenoic acid to the compound (I), and then extracting, isolating and purifying the compound (I) from the obtained fermented resultant. Ground plants of, for example, coffee, wheat, corn, tomato, mate, mugwort and burdock and extracts thereof may be mentioned as compositions containing 3-(4-hydroxy-3-methoxyphenyl)propenoic acid. Also, since 3-(4-hydroxy-3-methoxyphenyl)propenoic acid is a constituent of lignin in arboreous plants and herbaceous plants, lignin or compositions containing lignin may be also used as a raw material of fermentation. As microorganisms having phenolic acid reductases, lactic acid bacteria, etc. such as *Lactobacillus plantarum, Lactobacillus fermentum, Lactobacillus gasseri, Lactobacillus johnsonii, Lactobacillus crispatus, Lactobacillus acidophilus, Lactobacillus amylovorus, Lactobacillus delbrueckii, Lactobacillus buchneri, Lactobacillus kefiranofaciens, Lactobacillus gallinarum* and *Enterococus faecalis*, may be mentioned.

A method of extracting, isolating and purifying the compound (I) from the plants or fermented resultants above, etc. is not particularly limited and may be performed by normally used methods. An extracting treatment may be, for example, drying the plants or fermented resultants explained above as a raw material of extraction and putting the dried material into an extraction solvent for extraction or the dried material may be pulverized using a pulverizing machine before putting into the extraction solvent. It is possible to dry under the sun or by using a normally-used drying machine. Alternatively, a pretreatment of degreasing, etc. may be performed by using hexane or other nonpolar solvent before using it as a raw material of extraction. By performing a pretreatment like degreasing, an extracting treatment using a polar solvent can be performed efficiently.

As an extraction solvent, polar solvents are preferably used. For example, water and hydrophilic organic solvents may be mentioned, and one of them or in combination of two or more kinds may be used preferably at room temperature or at a temperature of a boiling point of the solvent or lower.

Water able to be used as the extraction solvent includes pure water, tap water, well water, mineral spring water, mineral water, hot spring water, spring water, fresh water and those subjected to a variety of treatments thereon. Treatments to be performed on the water include, for example, purification, heating, sanitization, filtration, ion exchange, osmotic pressure control and buffering, etc. Accordingly, water able to be used as the extraction solvent in the present embodiment also includes purified water, hot water, ion exchange water, physiological salt water, phosphate buffer solution and phosphate buffer physiological salt water, etc.

As hydrophilic organic solvents able to be used as the extraction solvent, methanol, ethanol, propyl alcohol, isopropyl alcohol and other C1-5 lower aliphatic alcohol; acetone, methyl ethyl ketone and other lower aliphatic ketones; 1,3-butylene glycol, propylene glycol, glycerin and other C2-5 polyhydric alcohol; etc. may be mentioned.

When using as the extraction solvent a mixed solution of two or more kinds of polar solvents, a mixing ratio thereof may be adjusted suitably. For example, when using as the extraction solvent a mixture of water and lower aliphatic alcohol, a mixing ratio of water and lower aliphatic alcohol is preferably 9:1 to 1:9 (volume ratio) and more preferably 7:3 to 2:8 (volume ratio). When using a mixed solution of water and a lower aliphatic ketone, a mixing ratio of water and lower aliphatic ketone is preferably 9:1 to 2:8 (volume ratio), and when using a mixed solution of water and polyhydric alcohol, a mixing ratio of water and polyhydric alcohol is preferably 8:2 to 1:9 (volume ratio).

The extraction treatment is not particularly limited as long as it is possible to elute soluble components contained in a raw material of extraction into an extraction solvent and may be performed by normally used methods. For example, an extract can be obtained by immersing a raw material for extraction in an extraction solvent in an amount of 5 to 15 times (in a mass ratio) the raw material, extracting soluble components at normal temperature or by heating under reflux and, then, filtering to remove extraction residue. When the solvent is distilled away from the obtained extract, a pasty condensed resultant is obtained, and when the condensed substance is furthermore dried, a dried substance is obtained.

A method of isolating and purifying the compound (I) from the thus obtained extract, condensed substance of the extract or dried substance of the extract obtained is not particularly limited and normally used methods may be used. For example, a method of dissolving the extract in a developing solvent and subjecting to column chromatography using a porous material, such as silica gel and alumina, or a porous resin, such as a styrene-divinylbenzene copolymer and polymethacrylate, etc. so as to collect a fraction including the compound (I) may be mentioned. Here, a developing solvent may be selected suitably in accordance with a stationary phase to be used. When separating an extract by normal phase chromatography using silica gel as a stationary phase, a developing solvent of chloroform and methanol in a ratio of 95:5, etc. may be mentioned. Furthermore, the fraction including the compound (I) obtained by column chromatography may be refined by using optional organic compound refining means, such as reverse phase silica gel chromatography using ODS, recrystallization, liquid-liquid coutercurrent extraction and column chromatography using an ion exchange resin.

Angiotensin-Converting Enzyme Inhibitor and Blood Pressure-Lowering Agent

Since the compound (I) obtained as explained above exhibits an excellent effect of inhibiting an angiotensin-converting enzyme, it can be used as an active ingredient of an angiotensin-converting enzyme inhibitor. Since the compound (I) also exhibits an excellent effect of lowering blood pressure, it can be also used as an active ingredient of a blood pressure-lowering agent.

In other words, the compound (I) can be used for producing an angiotensin-converting enzyme inhibitor and a blood pressure-lowering agent.

An angiotensin-converting enzyme inhibitor and a blood pressure-lowering agent of the present embodiment can be used for a wide range of purposes, such as pharmaceutical products, quasi-drugs and cosmetic products.

Although the blood pressure-lowering effect of the compound (I) is brought out, for example, based on the effect of inhibiting an angiotensin-converting enzyme, the blood pressure-lowering effect provided by the compound (I) is not limited to a blood pressure-lowering effect brought out based on the effect of inhibiting an angiotensin-converting enzyme.

Note that, instead of isolated compound (I), a composition containing the compound (I) may be also used as an active ingredient of an angiotensin-converting enzyme inhibitor and a blood pressure-lowering agent according to the present embodiment. Here, "a composition containing the compound (I)" in the present embodiment includes extracts obtained from plants containing the compound (I) as a raw material of extraction, fermented substances containing the compound (I) and extracts obtained from the fermented substances as raw material of extraction. The "extracts" include extracts in the form of liquid obtained by an extracting treatment, diluted or condensed solution of the extracts, and dried substances obtained by drying the extracts.

When using a composition containing the compound (I) as an active ingredient of an angiotensin-converting enzyme inhibitor and a blood pressure-lowering agent, the compound (I) in the composition is preferably 0.1 wt % or more, more preferably 5 wt % or more and particularly preferably 50 wt % or more. When using a substance with increased purity of the compound (I) as an active ingredient, it is possible to obtain an angiotensin-converting enzyme inhibitor and a blood pressure-lowering agent having furthermore excellent effects.

An angiotensin-converting enzyme inhibitor and a blood pressure-lowering agent of the present embodiment may be made only of the compound (I) or of a composition containing the compound (I). Alternatively, the component (I) or a composition containing the compound (I) may be pharmaceutically prepared.

An angiotensin-converting enzyme inhibitor and a blood pressure-lowering agent of the present embodiment may be pharmaceutically prepared into any forms, such as powder, granule, tablet and liquid, by using pharmaceutically acceptable carriers, such as dextrin and cyclodextrin, and other optional auxiliaries by normally used methods. Here, as auxiliaries, for example, an excipient, binder, disintegrant, lubricant, stabilizer and corrigent may be used. An angiotensin-converting enzyme inhibitor and a blood pressure-lowering agent may be blended into other compositions (for example, skin cosmetics and hair cosmetics) to be used and also used as ointments, liquids for external use and plasters, etc.

When pharmaceutically preparing the angiotensin-converting enzyme inhibitor and a blood pressure-lowering agent of the present embodiment, a content of the compound (I) or a composition containing the compound (I) is not particularly limited and may be determined suitably in accordance with the purposes.

As needed, other natural extracts, etc. having the effect of inhibiting an angiotensin-converting enzyme and the effect of lowering bool pressure may be blended together with the compound (I) or with a composition containing the compound (I) and used as an active ingredient in the angiotensin-converting enzyme inhibitor and blood pressure-lowering agent of the present embodiment.

To patients, transdermal administration and oral administration, etc. may be mentioned as administration methods of the angiotensin-converting enzyme inhibitor and blood pressure-lowering agent of the present embodiment, and a suitable method may be selected in accordance with a kind of disease for its prevention or treatment, etc. Also, a dose of the angiotensin-converting enzyme inhibitor and blood pressure-lowering agent of the present embodiment may be adjusted suitably in accordance with a kind of disease, severity, individual difference of the patient, an administration method and administration period, etc.

The angiotensin-converting enzyme inhibitor of the present embodiment suppresses a reaction of generating angiotensin II by isolating C-terminal dipeptides of angiotensin I due to an action of inhibiting an angiotensin-converting enzyme provided by the compound (I) as an active ingredient. As a result of suppressing generation of angiotensin II, contraction of vascular smooth muscle is suppressed and blood pressure can be lowered. Note that, in addition to the use purposes above, the angiotensin-converting enzyme inhibitor of the present embodiment can be used for all purposes, wherein the effect of inhibiting an angiotensin-converting enzyme is significant.

The blood pressure-lowering agent of the present embodiment is capable of suppressing a reaction of generating angiotensin II by isolating C-terminal dipeptides of angiotensin I due to the effect of lowering blood pressure provided by the compound (I) as an active ingredient. As a result, the blood pressure-lowering agent of the present embodiment is capable of preventing or ameliorating hypertension and a variety of diseases relating to organopathy, etc. associated with hypertension, such as heart failure and myocardial infraction in heart, nephropathy and renal dysfunction in kidneys, and obstructive and dissociated arterial diseases. Note that in addition to the use purposes above, the blood pressure-lowering agent of the present embodiment can be used for all purposes, wherein the effect of inhibiting an angiotensin-converting enzyme is significant.

Since the angiotensin-converting enzyme inhibitor and blood pressure-lowering agent of the present embodiment have excellent effects of inhibiting an angiotensin-converting enzyme and lowering blood pressure, they can be used suitably as reagents for studies relating to the actions and mechanisms above, as well.

Beverages and Food Products for Inhibiting Angiotensin-Converting Enzyme and Lowering Blood Pressure Since the compound (I) has excellent effects of inhibiting an angiotensin-converting enzyme and lowering blood pressure, they may be blended suitably in beverages and food products. Here, the compound (I) may be blended as it is, or an angiotensin-converting enzyme inhibitor or a blood pressure-lowering agent obtained by pharmaceutically preparing the compound (I) may be blended.

By blending the compound (I) or by blending an angiotensin-converting enzyme inhibitor or blood pressure-lowering agent obtained by pharmaceutically preparing the compound (I), beverages and food products suitable for the purpose of inhibiting an angiotensin-converting enzyme or lowering blood pressure can be provided. It is preferable because the actions above are brought out more effectively when added to beverages and food products.

Here, beverages and food products are defined as those having no harm on human health and taken orally or through digestive canal in normal social life and are not restricted by administrative classifications, namely, foods, pharmaceuticals and quasi-drugs, etc. In other words, "beverages and food products" in the present embodiment widely include foods in general, health foods (beverages and foods with functional claims), foods with health claims (foods for specific health uses and foods with nutrient function claims), quasi-drugs and pharmaceutical products, etc. It is preferable that beverages and food products according to the present embodiment are those which can indicate thereon or on their packages the preferable actions, that the compound (I) provides, and it is particularly preferable if they are foods with health claims (foods for specific health uses, foods with function claims and foods with nutrient function claims), quasi-drugs and pharmaceutical products.

When blending beverages and food products with the compound (I) or an angiotensin-converting enzyme inhibitor or a blood pressure-lowering agent obtained by pharmaceutically preparing the compound (I), a blending amount of the active ingredient therein may be changed suitably considering a use purpose, symptoms and gender, etc. and it is preferable that an intake of extract per day becomes approximately 1 to 1000 mg for adults in consideration of general intake of the object beverage or food to be added to. On the other hand, when the object beverage or food to be added to is in the form of granule, tablet or capsule, an adding amount of the compound (I) or an angiotensin-converting enzyme inhibitor or a blood pressure-lowering agent obtained by pharmaceutically preparing the compound (I) is normally 0.1 to 100 wt % with respect to the object beverage or food product to be added to, and preferably 5 to 10 wt %.

Beverages and food products of the present embodiment may be any beverage or food blended with the compound (I) as long as activeness thereof is not hindered or may be nutrition supplemental food containing the compound (I) as its main ingredient.

When producing the beverages and food products of the present embodiment, optional auxiliaries, such as dextrin, starch and other saccharides; gelatin, soybean protein, corn protein and other proteins; alanine, glutamine, isoleucine and other amino acids; cellulose, gum arabic and other polysaccharides; soybean oil, medium chain fatty acid triglycerides and other oil and fat, may be added so as to obtain beverage and food in any optional form.

Beverages and food products to be blended with the compound (I) are not particularly limited and, to list specific examples, refreshing beverages, carbonated beverages, nutrient beverages, fruit beverages, lactic beverages and other beverages (including concentrated stock solution and powder for preparation); ice cream, ice sorbet, shaved ice and other frozen desserts; buckwheat noodle, udon noodle, harusame (gelatin noodle), wrapping skin of jiaozi dumpling, wrapping skin of shaomai dumpling, Chinese noodle, instant noodle and other noodles; candy, chewing gum, chocolate, tablet-shaped confectionery, snack food, biscuits, jelly, jam, cream, baked confectioneries and other confectioneries; fish cakes, ham, sausages and other processed foods of fishery products and livestock products; processed milk, fermented milk and other dairy products; salad oil, tempura oil, margarine, mayonnaise, shortening, whipped cream, dressing, other oil and fat, and processed foods of oil and fat; sauces, dipping and other seasonings; soups, stews, salads, ready-to-eat side dishes, pickles and other variety of health and nutritive supplemental foods; tablets, capsule preparations and drinkable preparations, etc. may be mentioned. When blending the compound (I) into these beverages and food products, normally-used auxiliary materials or additives may be used together.

The angiotensin-converting enzyme inhibitor, blood pressure-lowering agent, beverages and food products for inhibiting an angiotensin-converting enzyme, and beverages and food products for lowering blood pressure of the present embodiment may be suitably used for human, however, as long as the respective actions and effects are brought out, they can be applied also to animals besides human (for example, mice, rats, hamsters, dogs, cats, cows, pigs and monkeys).

EXAMPLES

Below, the present invention will be explained specifically by showing test examples, however, the present invention is not limited to the examples below. Note that, as a sample to be tested in the present test examples, a compound (I), which is 3-(4-hydroxy-3-methoxyphenyl)propionic acid (sample 1) produced by Tokyo Chemical Industry Co., Ltd., was used.

[Test Example 1] Test of Effect of Inhibiting Angiotensin-Converting Enzyme Conducted on Compound (I)

The effect of inhibiting an angiotensin-converting enzyme was tested on the compound (I) (sample 1) as explained below.

A sample solution (sample 1), obtained by suitably dissolving in and diluting with distilled water, and distilled water respectively in an amount of 50 μL were dispensed into test tubes (10 mL). A substrate solution was dispensed respectively in an amount of 250 μL and mixed. The test tubes were preheated in a thermostatic water-tank at 37° C. for 5 minutes. The preheated test tubes were added with an ACE solution in an amount of 100 μL, agitated immediately and brought to react in the thermostatic water-tank at 37° C. for 45 minutes. After the reaction finished, 3% metaphosphate solution in an amount of 3.6 mL was added and agitated to end reaction. The inactivated solution was subjected to HPLC analysis and isolated hippuric acid was measured. Based on a hippuric acid peak area and solid amount (concentration and weighed amount) from the HPLC, an ACE inhibition rate (%) was obtained. Then, concentration of the sample in the reaction solution, when exhibiting an ACE inhibition rate of 50%, ($IC_{50}$) was obtained.

The results are shown in Table 1.

A substrate solution was prepared to obtain a boric acid buffering solution (pH 8.3) with 8 mM substrate (Hippuryl-His-Leu produced by PEPTIDE INSTITUTE, INC.) and 640 mM sodium chloride. An ACE solution was prepared to obtain a boric acid buffering solution with 30 mU/mL ACE (produced by Sigma-Aldrich Co. LLC).

<Liquid Chromatography Condition >

Column: Wakosil-II 5C18 HG (4.5mm I.D.×150mm produced by Wako Pure Chemical Industries, Ltd.)

Column Temperature: 40° C.

Mobile Phase: 20 mM $KH_2PO_4 \cdot H_3PO_4$ (pH 3.0): Methanol (57:43, v/v)

Flow Rate: 1.0 mL/min.

Detection Wavelength: 228 nm

Feed Amount: 20 μL

TABLE 1

| Sample Concentration (μg/mL) | ACE Inhibition Rate (%) | $IC_{50}$ (μg/mL) |
|---|---|---|
| 943.25 | 21.6 | 2142 |
| 1886.50 | 41.1 | |
| 3773.00 | 73.2 | |

As shown in Table 1, the compound (I) (sample 1) was confirmed to have an excellent effect of inhibiting an angiotensin-converting enzyme.

Combination Example 1

By using a normally-used method, tablets having a composition below were prepared.

| | |
|---|---|
| Compound (I) | 5.0 mg |
| Dolomite (containing 20% calcium and 10% magnesium) | 83.4 mg |
| Casein Phosphopeptide | 16.7 mg |
| Vitamin C | 33.4 mg |
| Maltitol | 136.8 mg |
| Collagen | 12.7 mg |
| Sucrose Fatty Acid Ester | 12.0 mg |

Combination Example 2

By using a normally-used method, oral liquid preparation having a composition below was prepared.
<Composition in One Ample (100 mL in one ample) >

| | |
|---|---|
| Compound (I) | 0.3 wt % |
| Sorbitol | 12.0 wt % |
| Sodium Benzoate | 0.1 wt % |
| Flavoring Agent | 1.0 wt % |
| Calcium Sulfate | 0.5 wt % |
| Purified Water | the rest (100 wt %) |

INDUSTRIAL APPLICABILITY

An angiotensin-converting enzyme inhibitor and a blood pressure-lowering agent of the present invention can contribute largely to ameliorating hypertension, etc.

The invention claimed is:

1. A method for inhibiting angiotensin-converting enzyme in a patient in need of inhibiting angiotensin-converting enzyme, comprising:

preparing a composition containing a compound represented by formula (I) as an angiotensin-converting enzyme inhibitor, and (I)

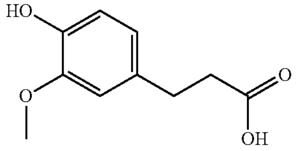

administering the composition containing an effective amount of the compound represented by formula (I) to the patient for inhibiting angiotensin-converting enzyme in the patient in need of inhibiting angiotensin-converting enzyme.

2. The method for inhibiting angiotensin-converting enzyme in a patient in need of inhibiting angiotensin-converting enzyme according to claim 1, wherein the compound represented by formula (I) is contained in a beverage or food product when administrated to the patient.

3. The method for inhibiting angiotensin-converting enzyme in a patient in need of inhibiting angiotensin-converting enzyme according to claim 1, wherein the compound represented by formula (I) is 3-(4-hydroxy-3-methoxyphenyl) propionic acid.

4. The method for inhibiting angiotensin-converting enzyme in a patient in need of inhibiting angiotensin-converting enzyme according to claim 1, wherein the composition contains 0.1 wt % or more of the compound represented by formula (I).

5. A method for lowering blood pressure in a patient in need of lowering blood pressure, comprising:

preparing a composition containing a compound represented by formula (I) as a blood pressure-lowering agent, and (I)

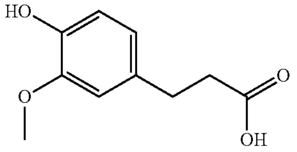

administering the composition containing an effective amount of the compound represented by formula (I) to the patient for lowering blood pressure of the patient in need of lowering blood pressure.

6. The method for lowering blood pressure in a patient in need of lowering blood pressure according to claim 5, wherein the compound represented by formula (I) is contained in a beverage or food product when administrated to the patient.

7. The method for lowering blood pressure in a patient in need of lowering blood pressure according to claim 5, wherein the compound represented by formula (I) is 3-(4-hydroxy-3-methoxyphenyl) propionic acid.

8. The method for lowering blood pressure in a patient in need of lowering blood pressure according to claim 5, wherein the composition contains 0.1 wt % or more of the compound represented by formula (I).

9. A method for inhibiting angiotensin-converting enzyme and lowering blood pressure in a patient in need of inhibiting angiotensin-converting enzyme and lowering blood pressure, the method comprising:

preparing a composition containing a compound represented by formula (I) as an angiotensin-converting enzyme inhibitor and a blood pressure-lowering agent, and (I)

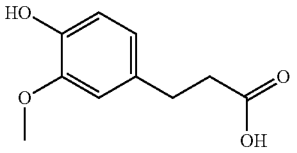

administering the composition containing an effective amount of the compound represented by formula (I) to the patient for inhibiting angiotensin-converting enzyme and for lowering blood pressure in the patient in need of inhibiting angiotensin-converting enzyme and lowering blood pressure.

10. The method for inhibiting angiotensin-converting enzyme and lowering blood pressure in a patient in need of inhibiting angiotensin-converting enzyme and lowering blood pressure according to claim 9, wherein the compound represented by formula (I) is 3-(4-hydroxy-3-methoxyphenyl) propionic acid.

11. The method for inhibiting angiotensin-converting enzyme and lowering blood pressure in a patient in need of inhibiting angiotensin-converting enzyme and lowering blood pressure according to claim 9, wherein the composition contains 0.1 wt % or more of the compound represented by formula (I).

12. The method for inhibiting angiotensin-converting enzyme and for lowering blood pressure in a patient in need of inhibiting angiotensin-converting enzyme and lowering blood pressure according to claim 9, wherein the compound represented by formula (I) is contained in a beverage or food product when administrated to the patient.

* * * * *